(12) United States Patent
Black

(10) Patent No.: US 7,378,056 B2
(45) Date of Patent: May 27, 2008

(54) CIRCUITS FOR IN VIVO DETECTION OF BIOMOLECULE CONCENTRATIONS USING FLUORESCENT TAGS

(75) Inventor: Robert D. Black, Raleigh, NC (US)

(73) Assignee: Sicel Technologies, Inc., Morrisville, NC (US)

( * ) Notice: Subject to any disclaimer, the term of this patent is extended or adjusted under 35 U.S.C. 154(b) by 865 days.

(21) Appl. No.: 10/005,889

(22) Filed: Nov. 7, 2001

(65) Prior Publication Data

US 2002/0102212 A1    Aug. 1, 2002

Related U.S. Application Data

(60) Provisional application No. 60/247,574, filed on Nov. 9, 2000.

(51) Int. Cl.
*B32B 5/02* (2006.01)
(52) U.S. Cl. .............. 422/82.05; 422/82.08; 422/55; 422/99; 435/288.7; 600/486
(58) Field of Classification Search .......... 422/50, 422/55, 68.1, 82.05–82.08, 99; 435/7.1, 435/808, 288.7; 436/63, 164, 172; 356/73.1, 356/319; 600/486, 407
See application file for complete search history.

(56) References Cited

U.S. PATENT DOCUMENTS

| | | | |
|---|---|---|---|
| 3,229,684 A | 1/1966 | Nagumo et al. .............. 600/302 |
| 3,638,640 A | 2/1972 | Shaw ........................ 128/2 R |
| 3,972,320 A | 8/1976 | Kalman .................... 128/2.1 A |
| 4,163,380 A | 8/1979 | Masoner ...................... 72/342 |
| 4,326,535 A | 4/1982 | Steffel et al. ................ 128/631 |
| 4,361,153 A | 11/1982 | Slocum et al. ........... 128/419 P |
| 4,397,313 A | 8/1983 | Vaguine ..................... 128/399 |
| 4,397,314 A | 8/1983 | Vaguine ..................... 128/399 |
| 4,416,283 A | 11/1983 | Slocum ................ 128/419 PG |
| 4,431,004 A | 2/1984 | Bessman et al. ............ 128/635 |
| 4,484,076 A | 11/1984 | Thomson ................ 250/370.07 |
| 4,494,545 A | 1/1985 | Slocum et al. ............... 128/1.5 |
| 4,519,401 A | 5/1985 | Ko et al. ..................... 118/748 |
| 4,523,279 A | 6/1985 | Sperinde et al. ............ 364/416 |
| 4,541,901 A | 9/1985 | Parker et al. |
| 4,543,953 A | 10/1985 | Slocum et al. ......... 128/419 PT |
| 4,556,063 A | 12/1985 | Thompson et al. .... 128/419 PT |
| 4,571,292 A | 2/1986 | Liu et al. .................... 204/412 |
| 4,571,589 A | 2/1986 | Slocum et al. ........ 128/419 PG |
| 4,575,676 A | 3/1986 | Palkuti .................... 324/158 D |
| 4,625,733 A | 12/1986 | Säynäjäkan gas ........... 128/687 |
| 4,638,436 A | 1/1987 | Badger et al. .............. 364/414 |
| RE32,361 E | 2/1987 | Duggan ..................... 128/696 |
| 4,651,741 A | 3/1987 | Passafaro .................... 128/633 |
| 4,655,880 A | 4/1987 | Liu ............................. 204/1 T |
| 4,678,916 A | 7/1987 | Thomson .................... 250/370 |
| 4,681,111 A | 7/1987 | Silvian ................ 128/419 PT |
| 4,703,756 A | 11/1987 | Gough et al. ............... 128/635 |
| 4,719,919 A | 1/1988 | Marchosky et al. ........ 128/401 |
| 4,750,495 A | 6/1988 | Moore et al. ......... 128/419 PG |
| 4,769,547 A | 9/1988 | Uber, III .................... 250/374 |
| 4,793,825 A | 12/1988 | Benjamin et al. ........... 128/419 |
| 4,796,641 A | 1/1989 | Mills et al. ................. 128/748 |
| 4,804,847 A | 2/1989 | Uber, III ................. 250/370 F |
| 4,846,191 A | 7/1989 | Brockway et al. .......... 128/748 |
| 4,847,617 A | 7/1989 | Silvian .................. 340/970.16 |
| 4,900,422 A | 2/1990 | Bryan et al. ................ 204/401 |
| 4,919,141 A | 4/1990 | Zier et al. ................... 128/635 |
| 4,935,345 A | 6/1990 | Guilbeau et al. ............. 435/14 |
| 4,944,299 A | 7/1990 | Silvian ................ 128/419 PG |
| 4,958,645 A | 9/1990 | Cadell et al. ............... 128/903 |
| 4,961,422 A | 10/1990 | Marchosky et al. ........ 128/399 |
| 4,970,391 A | 11/1990 | Uber, III .................... 250/374 |
| 4,976,266 A | 12/1990 | Huffman et al. ............ 128/659 |
| 4,989,601 A | 2/1991 | Marchosky et al. ........ 128/399 |
| 5,008,546 A | 4/1991 | Mazziotta et al. .......... 250/366 |
| 5,012,411 A | 4/1991 | Policastro et al. ..... 364/413.06 |
| 5,098,547 A | 3/1992 | Bryan et al. ................ 204/401 |
| 5,109,850 A | 5/1992 | Blanco et al. .............. 128/635 |
| 5,117,113 A | 5/1992 | Thomson et al. ...... 250/370.07 |
| 5,117,824 A | 6/1992 | Keimel et al. ........ 128/419 PG |

(Continued)

FOREIGN PATENT DOCUMENTS

DE        3219558        12/1983

(Continued)

OTHER PUBLICATIONS

International Search Report for International Application Serial No. PCT/US01/47373; dated Aug. 6, 2002.

(Continued)

*Primary Examiner*—Long V. Le
*Assistant Examiner*—Gary W. Counts
(74) *Attorney, Agent, or Firm*—Myers Bigel Sibley & Sajovec, P.A.

(57) ABSTRACT

Methods are disclosed wherein labeled antibodies can be provided in vivo to tissue having antigens that specifically bind the labeled antibody. A first optical radiation is emitted into the tissue in vivo to excite the labeled antibody bound to the antigen in vivo. A second optical radiation that is emitted by the excited labeled antibody, in response to the excitation thereof, can be detected in vivo. Related telemetric circuits and compositions of matter are also disclosed.

16 Claims, 4 Drawing Sheets

U.S. PATENT DOCUMENTS

| | | | |
|---|---|---|---|
| 5,126,937 A | 6/1992 | Yamaguchi et al. | 364/413.11 |
| 5,127,404 A | 7/1992 | Wyborny et al. | 128/419 P |
| 5,137,022 A | 8/1992 | Henry | 128/419 PT |
| 5,159,262 A | 10/1992 | Rumbaugh et al. | 324/765 |
| 5,163,380 A | 11/1992 | Duffy et al. | 119/15 |
| 5,166,073 A | 11/1992 | Lefkowitz et al. | 436/57 |
| 5,186,172 A | 2/1993 | Fiddian-Green | 128/632 |
| 5,193,538 A | 3/1993 | Ekwall | 128/419 PT |
| 5,197,466 A | 3/1993 | Marchosky et al. | 128/399 |
| 5,205,294 A | 4/1993 | Flach et al. | 128/696 |
| 5,215,887 A | 6/1993 | Saito | 435/14 |
| 5,264,843 A | 11/1993 | Silvian | 340/870 |
| 5,309,085 A | 5/1994 | Sohn | 324/71.5 |
| 5,314,450 A | 5/1994 | Thompson | 607/32 |
| 5,318,023 A | 6/1994 | Vari et al. | 128/633 |
| 5,324,315 A | 6/1994 | Grevious | 607/60 |
| 5,330,634 A | 7/1994 | Wong et al. | 204/409 |
| 5,354,314 A | 10/1994 | Hardy et al. | 128/653 |
| 5,354,319 A | 10/1994 | Wyborny et al. | 607/32 |
| 5,355,880 A | 10/1994 | Thomas et al. | 128/653 |
| 5,372,133 A | 12/1994 | Hogen et al. | 128/631 |
| 5,377,676 A | 1/1995 | Vari et al. | 128/634 |
| 5,383,909 A | 1/1995 | Keimel | 607/5 |
| 5,425,361 A | 6/1995 | Fenzlein et al. | 128/635 |
| 5,431,171 A | 7/1995 | Harrison et al. | 128/698 |
| 5,444,254 A | 8/1995 | Thomson | 250/370.07 |
| 5,466,246 A | 11/1995 | Silvian | 607/32 |
| 5,470,345 A | 11/1995 | Hassler et al. | 607/36 |
| 5,476,488 A | 12/1995 | Morgan et al. | 607/30 |
| 5,480,415 A | 1/1996 | Cox et al. | 607/32 |
| 5,481,262 A | 1/1996 | Urbas et al. | 340/870.17 |
| 5,497,772 A | 3/1996 | Schulman et al. | 128/635 |
| 5,505,828 A | 4/1996 | Wong et al. | 205/777.5 |
| 5,507,786 A | 4/1996 | Morgan et al. | 607/27 |
| 5,517,313 A | 5/1996 | Colvin, Jr. | 356/417 |
| 5,535,752 A | 7/1996 | Halperin et al. | 128/670 |
| 5,538,005 A | 7/1996 | Harrison et al. | 128/698 |
| 5,545,187 A | 8/1996 | Bergstrom et al. | 607/31 |
| 5,549,113 A | 8/1996 | Halleck et al. | 128/633 |
| 5,549,654 A | 8/1996 | Powell | 607/25 |
| 5,556,421 A | 9/1996 | Prutchi et al. | 607/36 |
| 5,557,702 A | 9/1996 | Yoshikawa et al. | 385/143 |
| 5,562,713 A | 10/1996 | Silvian | 607/32 |
| 5,564,434 A | 10/1996 | Halperin et al. | 128/675 |
| 5,571,148 A | 11/1996 | Loeb et al. | |
| 5,572,996 A | 11/1996 | Doiron et al. | 128/633 |
| 5,591,217 A | 1/1997 | Barreras | 607/5 |
| 5,593,430 A | 1/1997 | Renger | 607/9 |
| 5,596,199 A | 1/1997 | McNulty et al. | 250/370.07 |
| 5,606,163 A | 2/1997 | Huston et al. | 250/337 |
| 5,620,472 A | 4/1997 | Rahbari | 128/903 |
| 5,620,475 A | 4/1997 | Magnusson | 607/30 |
| 5,620,479 A | 4/1997 | Diederich | 607/97 |
| 5,626,630 A | 5/1997 | Markowitz et al. | 607/60 |
| 5,626,862 A | 5/1997 | Brem et al. | 424/426 |
| 5,628,324 A | 5/1997 | Sarbach | 128/670 |
| 5,630,413 A | 5/1997 | Thomas et al. | 128/633 |
| 5,656,815 A | 8/1997 | Justus et al. | 250/337 |
| 5,681,611 A | 10/1997 | Yoshikawa et al. | 427/163.2 |
| 5,682,888 A | 11/1997 | Olson et al. | 128/653.1 |
| 5,720,771 A | 2/1998 | Snell | 607/60 |
| 5,732,704 A | 3/1998 | Thurston et al. | 128/659 |
| 5,744,804 A | 4/1998 | Meijer et al. | 250/369 |
| 5,744,805 A | 4/1998 | Raylman et al. | 250/370.01 |
| 5,759,199 A | 6/1998 | Snell et al. | 607/60 |
| 5,791,344 A | 8/1998 | Schulman et al. | 128/635 |
| 5,811,814 A | 9/1998 | Leone et al. | 250/368 |
| 5,814,089 A | 9/1998 | Stokes et al. | 607/32 |
| 5,833,603 A | 11/1998 | Kovacs et al. | 600/317 |
| 5,840,148 A | 11/1998 | Campbell et al. | 156/275.5 |
| 5,857,463 A | 1/1999 | Thurston et al. | 128/659 |
| 5,879,375 A | 3/1999 | Larson et al. | 607/30 |
| 5,891,179 A | 4/1999 | Er et al. | 607/27 |
| 5,916,167 A | 6/1999 | Kramer et al. | 600/436 |
| 5,918,110 A | 6/1999 | Abraham-Fuchs et al. | 438/48 |
| 5,928,150 A | 7/1999 | Call | 600/436 |
| 5,932,879 A | 8/1999 | Raylman et al. | 250/370.06 |
| 5,939,453 A | 8/1999 | Heller et al. | 514/452 |
| 5,987,350 A | 11/1999 | Thurston | 600/436 |
| 6,015,390 A | 1/2000 | Krag | 600/549 |
| 6,025,137 A | 2/2000 | Shyjan | 435/6 |
| D423,377 S | 4/2000 | Atterbury et al. | D10/47 |
| 6,047,214 A | 4/2000 | Mueller et al. | 607/61 |
| D424,453 S | 5/2000 | Atterbury et al. | D10/47 |
| 6,070,096 A | 5/2000 | Hayashi | 600/477 |
| 6,076,009 A | 6/2000 | Raylman et al. | 600/436 |
| 6,087,666 A | 7/2000 | Huston et al. | 250/484.5 |
| 6,093,381 A | 7/2000 | Triozzi et al. | 424/1.49 |
| 6,099,821 A | 8/2000 | Rich et al. | 424/1.61 |
| 6,172,368 B1 | 1/2001 | Tarr et al. | 250/370.07 |
| 6,217,869 B1* | 4/2001 | Meyer et al. | 424/178.1 |
| 6,239,724 B1 | 5/2001 | Doron et al. | 340/870.28 |
| 6,240,312 B1 | 5/2001 | Alfano et al. | 600/478 |
| 6,242,741 B1 | 6/2001 | Miller et al. | 250/363.02 |
| 6,259,095 B1 | 7/2001 | Bouton et al. | 250/336.1 |
| 6,272,373 B1 | 8/2001 | Bouton | 600/436 |
| 6,274,159 B1 | 8/2001 | Marotta et al. | 424/426 |
| 6,295,680 B1 | 10/2001 | Wahl et al. | 14/1 |
| 6,304,766 B1 | 10/2001 | Colvin, Jr. | 600/317 |
| 6,343,227 B1* | 1/2002 | Crowley | 600/407 |
| 6,363,940 B1 | 4/2002 | Krag | 128/899 |
| 6,444,475 B1 | 9/2002 | Anderson, Jr. et al. | 436/161 |
| 6,491,666 B1* | 12/2002 | Santini et al. | 604/191 |
| 6,551,838 B2* | 4/2003 | Santini et al. | 436/174 |
| 6,614,025 B2 | 9/2003 | Thomson et al. | 250/370.01 |
| 6,650,930 B2 | 11/2003 | Ding | 600/436 |
| 6,750,311 B1* | 6/2004 | Van Antwerp et al. | 528/77 |
| 2001/0051766 A1* | 12/2001 | Gazdzinski | 600/309 |
| 2002/0072784 A1* | 6/2002 | Sheppard et al. | 607/60 |

FOREIGN PATENT DOCUMENTS

| | | |
|---|---|---|
| DE | 3332075 | 3/1984 |
| DE | 4341903 | 6/1995 |
| EP | 0420177 A1 | 3/1991 |
| EP | 0471957 A2 | 2/1992 |
| EP | 0537761 A2 | 4/1993 |
| EP | 0245073 B1 | 12/1993 |
| EP | 0386218 B1 | 10/1996 |
| GB | 2263196 A | 7/1993 |
| WO | WO95/17809 | 6/1995 |
| WO | WO97/33513 | 9/1997 |
| WO | WO98/02209 A2 | 1/1998 |
| WO | WO98/43701 | 8/1998 |
| WO | WO98/58250 | 12/1998 |
| WO | WO99/48419 | 9/1999 |
| WO | WO99/58065 | 11/1999 |
| WO | WO99/63881 | 12/1999 |
| WO | WO00/18294 | 4/2000 |
| WO | WO00/29096 | 5/2000 |
| WO | WO00/33065 | 6/2000 |
| WO | WO 00/33065 | 6/2000 |
| WO | WO00/40299 | 7/2000 |
| WO | WO02/39917 | 11/2000 |
| WO | WO02/09775 | 2/2002 |
| WO | WO02/39918 | 5/2002 |
| WO | WO02/100485 | 6/2002 |

OTHER PUBLICATIONS

Braichotte et al.; *Clinical Pharmacokinetic Stuies of Photofrin by Fluorescence Spectroscopy in the Oral Cavity, the Esophagus, and the Bronchi*; Cancer; vol. 75, No. 11; Jun. 1, 1995; pp. 2768-2778.

Cortese et al.; *Clinical Application of a New Endoscopic Technique for Detection of In Situ Bronchial Carcinoma*; Mayo Clinic Proceedings; vol. 54; Oct. 1979; pp. 635-641.

Bergh, Van Den, H.; *On the Evolution of Some Endoscopic Light Delivery Systems for Photodynamic Therapy*; Endoscopy; May 1998; pp. 392-407.

Hirsch et al.; *Early Detection of Lung Cancer: Clinical Perspectives of Recent Advances in Biology and Radiology*; Clinical Cancer Research; vol. 7; Jan. 2001; pp. 5-22.

Kinsey et al.; *Endoscopic System for Simultaneous Visual Examination and Electronic Detection of Fluorescence*; Review of Scientific Instruments; vol. 51, No. 10; Oct. 1980; pp. 1403-1406.

Kulapaditharom et al.; *Performance Characteristics of Fluorescence Endoscope in Detection of Head and Neck Cancers*; Annals of Otology, Rhinology & Laryngol; vol. 110(1); Jan. 2001; pp. 45-52.

Mayinger et al.; *Light-induced Autofluorescence Spectroscopy for the Endoscopic Detection of Esophageal Cancer*; Gastrointestinal Endoscopy; vol. 54, No. 2; Aug. 2001; pp. 195-201.

Mayinger et al.; *Endoscopic Fluorescence Spectroscopy in the Upper GI Tract for the Detection of GI Cancer: Initial Experience*; The American Journal of Gastroenterology; vol. 96, No. 9; Sep., 2001; pp. 2616-2621.

Akin et al., *RF telemetry powering and control of hermetically sealed integrated sensors and actuators*, Proc. Solid-State Sensors & Actuators Workshop, Hilton Head, SC, pp 145-148 (1990).

Akin, T., K. Najafi, R.M. Bradley, *An implantable multichannel digital neural recording system for a micromachined sieve electrode*, Proc. Int. Conf. on Solid-State Sensors and Actuators, Stockholm, Sweden, vol. 1, pp. 51-54 (Jun. 1995).

Alecu et al., *Dose perturbations due to in vivo dosimetry with diodes* Radiotherapy and Oncology, pp. 289-291, vol. 42, (1997).

Barber et al., *Comparison of NaI(T1), CdTe, and Hg12 surgical probes*: physical characterization, Med. Phys., 18(3):373-381 (May-Jun. 1991).

Barthe, Jean, *Electronic dosimeters based on solid state detectors, Nuclear. Instruments.* and Methods in Physics Research Sec. B vol. 184, pp. 158-189 (2001).

Bergh, Van Den, H., *On the Evolution of Some Endoscopic Light Delivery Systems for Photodynamic Therapy*, Endoscopy, May 1998, pp. 392-407.

Berthold et al., *Method for in-situ detection of tritium in water*, McDermott Technology Inc./RDTPA 99-03, pp. 1-9 (Sep. 19-22, 1999).

Biotelemetrics, Inc., 6520 Contempo Lane, Boca Raton, Florida 33433, Tel: 407-394-0315. Biotelemetry Page, http://speed.nimh.nih.gov/telemetry/classx.html, Feb. 1997.

Blackstock et al., *Tumor retention of 5-fluorouracil following irradiation observed using 19F nuclear magnetic resonance spectroscopy*, Init J Radiat Oncol Biol Phys, 36(3):641-648 (Oct. 1, 1996).

Bojsen et al., *A portable external two-channel radiotelemetrical GM-detector unit, for measurements of radionuclide-tracers in vivo*, Int J Appl Radiat Isot, 25(4):161-166 (Apr. 1974).

Bojsen et al., *A radiotelemetrical measuring device, implantable on animals*, for long term mersurements of radionuclide tracers, Int J Appl Radiat Isot, 23(11):505-511 (Nov. 1972).

Braichotte et al., *Clincal Pharmacokinetic Studies of Photofrin by Fluorescence Spectroscopy in the Oral Cavity*, the Esophagus, and the Bronchi, Cancer, vol. 75, No. 11, Jun. 1, 1995, pp. 2768-2778.

Brochure, *Be as smart as you can be with BMDS and Smart Alec™ your partners in intelligence*, Bio Medic Data Systems, Inc. (®1999).

Brochure, Come along for the incredible journey in the development of the IPTT-200, Bio Medic Data Systems, Inc. (®2000).

Butson, Martin J. et al, *A new radiotherapy surface dose detector: The MOSFET*, Medical Physics, American Institute of Physics, vol. 23 (5) pp 655-658 (May 1996).

Cortese et al., *Clinical Application of a New Endoscopic Technique for Detection of In Situ Bronchial Carcinoma*, Mayo Clinic Proceedings, vol. 54, Oct. 1979, pp. 635-641.

Cosofret et al., *Microfabricated sensor arrays sensitive to pH and K+ for ionic distribution measurements in the beating heart*, Analytical Chemistry, vol. 67, pp. 1647-1653 (1995).

Daghighian et al., *Intraoperative beta probe: a device for detecting tissue labeled with positron or electron emitting isotopes during surgery*, Med Phys, 21(1):153-157 (Jan. 1994).

Data Sciences International, http://www.ispex.ca/companies/instrumentation/DataScInt.html, Profile web pp. 1-2 and Instrumental Products 1-7, Copyright Ispex Exchange Inc., 2003, for examination purposes, applicant admits similar devices were available prior to earlier filing date of application.

Deutsch, S., *Fifteen-electrode time-multiplex EEG telemetry from ambulatory patients*, IEEE Transactions on Biomedical Engineering, vol. BME-26, pp. 153-159 (1979).

Dewhirst et al., *Soft-Tissue Sarcomas: MR Imaging and MR Spectroscopy for Prognosis and Therapy Monitoring, Radiology*, 174:847-853 (1990).

Dewhirst, *Concepts of oxygen transport at the microcirculatory level*, Seminars in Radiation Oncology, vol. 8, 1998, pp. 143-150.

Dienes et al., *Radiation Effects in Solids, Interscience Monographs in Physics and Astronomy*, vol. II, Interscience Publishers, Inc., pp. 1-4, 56-85, 90-122 and 129-177 (©1957).

Dimitrakopoulou et al., *Studies with Positron Emission Tomography After Systemic Adminstration of Fluorine-18-Uracil in Patients with Liver Metastases from Colorectal Carcinoma*, J Nucl Med, 34:1075-1081 (Jul. 1993).

Farrar IV Harry et al., *Gamma-Ray Dose Mapping in Operational Candu Reactor Containment Areas Using MOS Dosimeters*, pp. 441-446, Reactor Dosimetry, ASTM, 1994.

Fernald, *A microprocessor-based system for the fast prototyping of implantable instruments for biomedical research applications*, Doctoral Dissertation, Elec. & Computer Eng., NC State Univ., (1992).

Fernald, K., T. Cook, T. Miller, III, J. Paulos, *A microprocessor-based implantable telemetry systems*, Computer, vol. 24, No. 7, pp. 23-30 (1991).

Fisher, DR, *Radiation dosimetry for radioimmunotherapy. An overview of current capabilities and limitations*, Cancer, 73(3 Suppl):905-911 (Feb. 1, 1994).

Fryer, T., H. Sndler, W. Freund, E. McCutcheon, E. Carlson, *A multichannel implantable telemetry system for flow, pressure, and ECG measurements*, Jour. of Applied Physiology, vol. 39, pp. 318-326 (1973).

Gelezunas et al., *Silicon avalanche radiation detectors: the basis for a new ini vivo radiation detection probe*, Eur J Nucl Med, 8(10):421-424 (1983).

Gerweck, *Tumor pH: Implications for Treatment and Novel Drug Design*, 8 Seminars in Radiation Oncology, No. 5, pp. 176-182 (Jul. 1998).

Gilligan et al., *Evaluation of a subcutaneous glucose sensor out to 3 months in a dog model*, Diabetes Care, vol. 17, pp. 882-887 (1994).

Griffiths et al., *The OxyLite: a fibre-optic oxygen sensor*, British J. of Radiology, vol. 72, pp. 627-630 (1999).

Gschwend, S., J. Knutti, H. Allen, J. Meindl, *A general-purpose implantable multichannel telemetry system for physiological research*, Biotelemetry Patient Monitoring, vol. 6, pp. 107-117 (1979).

Hamburger et al., *Primary Bioassay of Human Tumor Stem Cells*, Science, 197:461-463 (1977).

Hansen, B., K. Aabo, J. Bojsen, *An implantable, externally powered radiotelemetric system for long-term ECG and heart-rate monitoring*, Biotelemetry Patient Monitoring, vol. 9., pp. 228-237 (1982).

Hassan et al., *A radiotelemetry pill for the measurement of ionizing radiation using a mercuric iodide detector*, Phys med Biol, 23(2):302-308 (Mar. 1978).

Heij et al., *Intraoperative search for neuroblastoma by MIBG and radioguided surgery with the gamma detector*, Med Pediatr Oncol, 28(3):171-174 (Mar. 1997).

Hines, *Advanced Biotelemetry Systems for Space Life Science*: PH Telemetry, Biotelementry XIII, Mar. 26-31, pp 131-137 (1995).

Hirsch et al. Early Detection of Lung Cancer: *Clinical Perspectives of Recent Advances in Biology and Radiology*, Clinical Cancer Research, vol. 7, Jan. 2001, pp. 5-22.

Hoffman et al., *Intraoperative probes and imaging probes*, Eur Jnl Nucl Med, 26(8):913-935 (Aug. 1999).

Holmstrom, N., P. Nilsson, J. Carlsten, S. Bowald, *Long-term in vivo experience of an electrochemical sensor using the potential step technique for measurement of mixed venous oxygen pressure*, Biosensors & Bioelectronics, 13, pp. 1287-1295 (1998).

Jornet et al., *Calibration of semiconductor detectors for dose assessment in total body irradiation*, Radiotherapy and Oncology, pp. 247-251, vol. 38, (1996).

Kastrissios et al., *Screening for Sources of Interindividual Pharmacokinetic Variability in Anticancer Drug Therapy*: Utility of Population Analysis, Cancer Investigation, 19(1):57-64 (Jan. 30, 2001).

Kern, D.H., *Tumor Chemosensitivity and Chemoresistance Assays*, Cancer 79(7):1447-1450 (1997).

Khouri et al., *An implantable semiconductor beta-radiation detector*, Am J Physiol, 232(1):H95-98 (Jan. 1977).

Kinsey et al., *Endoscopic System for Simultaneous Visual Examination and Electronic Detection of Fluorescence*, Review of Scientific Instruments, vol. 51, No. 10, Oct. 1980, pp. 1403-1406.

Kissel et al., *Noninvasive determination of the arterial input function of an anticancer drug from dynamic PET scans using the population approach*, Med Phys 26(4):609-615 (Apr. 1999).

Konigsberg Instruments, Inc., http://guide.labanimal.com/guide/companyjsp?b=3930, Lab Animal p. 1, Product Categories p. 1, Lab Animal Buyers Guide 2003 p. 1 and Animal Research Equipment pp 1-12, Nature Publishing Group, 2003, for examination purposes, applicant admits similar devices were available prior to earlier filing date of application.

Koutcher et al., *Potentiation of a Three Drug Chemotherapy Regimen by Radiation*, Cancer Res, 53:3518-3523 (1993).

Kulapaditharom et al., *Performance Characteristics of Fluorescence Endoscope in Detection of Head and Neck Cancers*, Annals of Ontology, Rhinology & Laryngol, vol. 110(1), Jan. 2001, pp. 45-52.

Lambrechts, M., Sansen, W., *Biosensors: Microelectrochemical Device*, NY, NY: IOP Publishing Ltd., pp. 206-208 (1992).

Loncol et al., *Entrance and exit dose measurements with semiconductors and thermoluminescent dosemeters: a comparison of methods and in vivo results*, Radiotherapy and Oncology, pp. 179-187 vol. 41, (1996).

Lowe, S., et al., *p53 status and the efficacy of cancer therapy in vivo*, Sci., vol. 266, pp. 807-810 (1994)..

Ma et al., *The photosensitizing effect of the photoproduct of protoporphyrin IX*, J. Photochem Photobiol B, Jul. 2001, vol. 60 (2-3), pp. 108-113.

Mackay, *Bio-Medical Telemetry, Sensing and Transmitting Biological Information from Animals and Man*, Second edition. New York, NY: IEEE Press (1993).

Marzouk et al., *Electrodeposited Iridium Oxide pH Electrode for Measurements of Extracellular Myocardial Acidosis during Acute Ischemia*, Anal. Chem., vol. 70, pp. 5054-5061 (1998).

Mathur, V.K, *Ion storage dosimetry*, Nuclear Instruments and Methods in Physics Research B, vol. 184 pp 190-206 (2001).

Mayinger et al., *Endoscopic Fluorescence Spectroscopy in the Upper GI Tract for the Detection of GI Cancer: Initial Experience*, The American Journal of Gastroenterology, vol. 96, No. 9, Sep. 2001, pp. 2616-2621.

Mayinger et al., *Light-induced Autofluorescence Spectroscopy for the Endoscopic Detection of Esophageal Cancer*, Gastrointestinal Endoscopy, vol. 54, No. 2, Aug. 2001, pp. 195-201.

Miller et al., *Clinical Molecular Imaging*, J Amer Coll Radiol 2004, 1, pp. 4-23.

Mittal et al., *Evaluation of an Ingestible Telemetric Temperature Sensor for Deep Hyperthermia Applications*, Int. J. Radiation Oncology Biol. Phys., vol. 21, pp. 1353-1361 (1991).

Moreno, D.J. et al., *A Simple Ionizing Radiation Spectrometer/ Dosimeter based on Radiation Sensing Field Effect Transistors (RadFETs)* Transducers '97 International Conference on Solid-State Sensors and Actuators Chicago, pp. 1283-1286 (Jun. 16-19, 1997).

Mueller, J. S., H. T. Nagle, Feasiblity of inductive powering of miniature low-power biotelemetry for use with microfabricated biomedical sensors, Proc. Biotelemetry XIII, Williamsburg, VA, Mar., pp. 372-377 (1995).

Myeck et al., *Colonic polyp differentiation using time-resolved autofluorescence spectroscopy*, Gastrointest. Endosc., Oct. 1998, No. 48(4), pp. 390-394.

National Aeronautics and Space Adminstration, *Extravehicular Activity Radiation Monitoring (EVARM)*, Fact Sheet FS 2001-11-191-MSFC, abstract review, Oct. 2001.

Olthuis, W., Bergveld, P., *Simplified design of the coulometric sensor-actuator system by the application of a time-dependent actuator current*, Sensors and Actuators B, vol. 7, pp. 479-483 (1992).

Oshima et al, *Development of Micro-Telemetering Multi-Sensor Capsule System with newly developed LSI for the clinical applications*, Transducers '87, The 4th International Conference on Solid-State Sensors and Actuators, pp 163-166 (1987).

Pauley, Donald J., R. Martin *A microminiature hybrid multichannel implantable biotelemetry system*, Biotelemetry Patient Monitoring, vol. 8, pp. 163-172 (1981).

PCT International Search Report, International Application No. PCT/US01/47373 dated Aug. 6, 2002.

PCT International Search Report, International Application No. PCT/US02/12855 dated Dec. 16, 2002.

PCT International Search Report, International Application No. PCT/US02/38111.

Pendower, J., *Disappearance of Gall-stones*, Medical Memoranda, British Medical Journal, pp. 492, 1964.

Piwnica-Worms et al., *Functional Imaging of Multidrug-resistant P-Glycoprotein with an Organotechnitium Complex*, Cancer Res, 53:977-984 (1993).

Presant et al., Enhancement of Fluorouracil Uptake in Human Colorectal and Gastric Cancers by Interferon or by High-Dose Methotrexate: An In Vivo Human Study Using Noninvasive[19] *F-Magnetic Resonance Spectroscopy*, J Clin Oncol, 18:255-261 (2000) Jan. 4, 1999.

Presant et al., *Human tumor fluorouracil trapping: clinical correlations of in vivo 19F nuclear magnetic resonance spectroscopy pharmacokinetics*, J Clin Oncol, 8(11):1868-1873 (Nov. 1990).

Puers, B., P. Wouters, M. DeCooman, *A low power multi-channel sensor interface for use in digital telemetry*, Sensors and Actuators A, vols. 37-28, pp. 260-267 (1993).

Ranii, D., N&O Article, *Company's device aims to monitor disease from inside.*, Mar. 30, 2000.

Ranii, D., N&O Article, *Sicel seeks go-ahead for clinical trials*. Apr. 17, 2002.

Raylman et al., *Evaluation of ion-implanted-silicon detectors for use in intraoperative positron-sensitive probes*, Med Phys, 23(11):1889-1895(Nov. 1996).

Reece M.H. et al., *Semiconductor Mosfet Dosimetery*, Health Physics Society annual Meeting, pp. 1-14, 1988.

Rollins et al., *Potential new endoscopic techniques for the earlier diagnosis of pre-malignancy*, Best Pract. Res. Clin. Gastroenterol, Apr. 2001, vol. 15 (2), pp. 227-247.

Schantz et al., *In vivo native cellular fluorescence and histological characteristics of head and neck cancer*, Clin. Cancer Res., May 1998, vol. 4 (5), pp. 1177-1182.

Shortt, Dr. Ken et al., *A New Direct Reading Extremity Dosimeter—How the ED-1 Sensor works*, Health Physics Society Annual Meeting, Jul. 1994.

Small Business Innovation Research Program Phase One Grant Application entitled *An Implantable Multi-channel Systems for Monitoring Tumors*, submitted on or about Dec. 1996 to U.S. Public Health Service.

Small Business Innovation Research Program Phase One Grant Application entitled *An Implantable Multi-channel System for Monitoring Tumors*, resubmitted with revisions on or about Aug. 1997 to the National Institute of Health.

Small Business Innovation Research Program Phase One Grant Application entitled *An Implantable Multi-channel System for Monitoring Tumors*, resubmitted to the U.S. funding authority on or about Apr. 1998.

Soubra, M. et al., *Evaluation of a dual bias dual metal oxide-silicon semiconductor field effect transistor detector as radiation dosimeter*, American Assoc. Phys. Med., vol. 21, No. 4, pp. 567-572, Apr. 1994.

Stepp et al., *Fluorescence endoscopy of gastrointestinal disease: basic principles, techniques, and clinical experience*, Endoscopy, May 1998, vol. 30(4), pp. 379-386.

Stevens et al., *5-Flourouracil metabolism monitored in vivo by $^{19}F$ NMR*, Br J Cancer, 50:113-117 (1984).

Sweeney et al., *Visualizing the kinetics of tumor-cell clearance in living animals*, PNAS, vol. 96, No. 21, pp. 12044-12049, Oct. 12, 1999.

Tarr, N.G. et al., *A Floating Gate MOSFET Dosimeter Requiring No External Bias Supply*, Redecs 97. Fourth European Conference on Radiation and Its Effects on Components and Systems (Cat. No. 97th 8294), pp 277-281 (1998).

Taylor et al., *The Forces in the Distal Femur and the Knee During Walking and Other Activities Measured by Telemetry*, J. of Anthroplasty, vol. 13, No. 4, pp. 428-437 (1998).

Thomson, I. et al., *Radiation Dosimetry with MOS Sensors*, Radiation Protection Dosimetry, vol. 6, No. 1-4, Nuclear Technology Publishing, pp. 121-124, 1984.

UCL Christian de Duve Institute of Cellular Pathology, Ludwig Institute for Cancer Research, URL www.Icp.ucl.ac.be/report95/licr95.html (1995).

Von Hoff et al., *Selection of Cancer Chemotherapy for a Patient by an In Vitro Assay Versus a Clinician*, JNCI 82:110-116 (1990) Oct. 25, 1989.

Watanabe et al., *A Preliminary Report on Continuous Recording of Salivary pH Using Telemetry in an Edentulous Patient*, Int'l J. Proshodontics, vol. 12, No. 4, pp. 313-317 (1999).

Wayne, E. et al., *Treatment of Thyroid Disorders*, To-day's Drugs, British Medical Journal, pp. 493-496, Aug. 22, 1964.

Webster, Editor, *Design of Cardiac Pacemakers*, New York, NY: IEEE Press, pp. 155-157 (1995).

Williams et al., *Multipurpose chip for physiological measurements*, IEEE International Symposium on Circuits and Systems, vol. 4, pp. 255-258, Proc. (1994).

Wolf et al., *Potential of microsensor-based feedback bioactuators for biophysical cancer treatment*, Biosensors & Bioelectronics, vol. 12, pp. 301-309 (1997).

Wolf et al., *19F-MRS studies of fluorinated drugs in humans*, Adv Drug Deliv Rev, 41(1):55-74 (Mar. 15, 2000).

Wolf et al., *Non-invasive 19F-NMRS of 5-fluorouracil in pharmacokinetics and pharmacodynamic studies*, NMR Biomed 11(7):380-387 (Nov. 1998).

Wolf et al., *Tumor trapping of 5-fluorouracil: In vivo $^{19}F$ NMR spectroscopic pharmacokinetics in tumor-bearing humans and rabbits*, Proc Natl Acad Sci USA, 87:492-496 (Jan. 1990).

Woolfenden et al., *Radiation detector probes for tumor localization using tumor-seeking radioactive tracers*, AJR Am J Roentgenol, 153(1):35-39 (Jul. 1989).

Wouters, P., M. De Cooman, R. Puers, *multi-purpose CMOS sensor interface for low-power applications, IEEE Journal of Solid-State Circuits*, vol. 29, No. 8, pp. 952-956 (Aug. 1994).

Yang et al., *Visualizing gene expression by whole-body fluorescence imaging*, PNAS, vol. 97, No. 22, pp. 12278-12282, Oct. 24, 2000.

Yarnell et al., *Drug Assays on Organ Cultures of Biopsies from Human Tumours*, Br Med J 2:490-491 (1964).

Young, R. C., V. T. DeVita, *Cell cycle characteristics of human solid tumors in vivo*, Cell Tissue Kinetics, vol. 3, pp. 285-290 (1970).

Zanzonico et al., *The intraoperative gamma probe: basic principles and choices available*, Semin Nucl Med 30 (1):33-48 (Jan. 2000).

Zonios, et al., *Diffuse reflectance spectroscopy of human adenomatous colon polyps in vivo*, Applied Optics, Nov. 1999, vol. 1; 38 (31), pp. 6628-6637.

Zuckier et al., *Remotely Pollable Geiger-Muller Detector for Continuous Monitoring of Iodine-131 Therapy Patients*, J. of Nuclear Med., vol. 39, No. 9, pp. 1558-1562 (Sep. 1998).

\* cited by examiner

CIRCUITS FOR IN VIVO DETECTION OF BIOMOLECULE CONCENTRATIONS USING FLUORESCENT TAGS

CLAIM FOR PRIORITY AND CROSS-REFERENCE TO RELATED APPLICATIONS

The present application claims priority to U.S. Provisional Application No. 60/247,574 filed Nov. 9, 2000, entitled Methods, Circuits, and Compositions of Matter for In Vivo Detection of Biomolecule Concentrations Using Fluorescent Tags, the entire disclosure of which is hereby incorporated herein by reference.

FIELD OF THE INVENTION

The present invention relates to the field of sensors, and more particularly, to biomolecular sensors.

BACKGROUND OF THE INVENTION

The ex vitro study of malignant cell populations has established some general principles by which clinical treatment protocols are developed. These principles have established differences between malignant and normal cell populations and have been employed in the treatment of malignant disease. There have been attempts to exploit these differences, both in pre-clinical and clinical studies, to obtain total tumor cell kills and improved cure rates.

One of the major obstacles in achieving this goal has been the difficulty in minimizing normal tissue toxicity while increasing tumor cell kill (therapeutic index). Thus, some treatment strategies employ an empirical approach in the treatment of malignant disease. In particular, the time of delivery and dose of cytotoxic agents can be guided more by the response and toxicity to normal tissue than by the effects on the malignant cell population.

Unfortunately, this approach may not provide accurate information on the changes during treatment of a malignant cell population. Making this information available may allow clinicians to exploit the differences between malignant and normal cells, and hence improve the treatment procedures.

There have been a number of attempts to study changes that occur within a cell population. However, these attempts have not shown the ability to monitor the changes on a real time basis. Indeed, these methods typically provide information at one point in time and most are designed to provide information on one particular function or parameter. In addition, most of the conventional methods can be expensive as well as time consuming. This can be problematic for patients undergoing extended treatment periods typical of radiation and chemotherapy, especially when it is desirable to follow changes both during an active treatment and subsequent to the active treatment.

In addition, tumors may have periods in which they are more susceptible to treatment by radiation or drug therapy. Providing a monitoring system which can continuously or semi-continuously monitor and potentially identify such a susceptible condition could provide increases in tumor destruction rates.

Numerous tumor specific antigens (TSA) have been identified and antibodies specific for a number of these TSA's are known. For example, it has been demonstrated that sigma-2 receptors found on the surface of cells of the 9L rat brain tumor cell line, the mouse mammary adenocarcinoma lines 66 (diploid) and 67 (aneuploid), and the MCF-7 human breast tumor cell line may be markers of tumor cell proliferation. See Mach R H et al., Sigma 2 receptors as potential biomarkers of proliferation in breast cancer. Cancer Res 1997 Jan. 1; 57(1):156-61; Al-Nabulsi I et al., Effect of ploidy, recruitment, environmental factors, and tamoxifen treatment on the expression of sigma-2 receptors in proliferating and quiescent tumour cells. Br J Cancer 1999 November; 81(6):925-33. Such markers may be amenable to detection by non-invasive imaging procedures. Accordingly, ligands that selectively bind sigma-2 receptors may be used to assess the proliferative status of tumors, although in vivo techniques utilizing such ligands have heretofore not been known. Although the field of tumor-specific treatment is still relatively unsettled, various researchers have proposed several potentially important techniques useful in such treatment. For example, the ex vitro detection of biomolecules can be useful in predicting the timing for advantageous treatment of tumors. Many of these techniques use a "hybridization event" to alter the physical or chemical properties associated with the biomolecules. The biomolecules having the altered property can be detected, for example, by optical or chemical means.

One known technique for the detection of biomolecules, called Enzyme-Linked Immunosorbent Assay (ELISA), involves the detection of binding between a biomolecule and an enzyme-labeled antibody specific for the biomolecule. Other methods of detecting biomolecules utilize immunofluorescence, involving the use of a fluorescently labeled antibody to indicate the presence of the biomolecule. The in vivo use of these techniques may involve an invasive introduction of a sensor into the in vivo site to be analyzed. Moreover, these techniques may not be reliable if the surface where the sensor and the tissue interact is not clean. In particular, in vivo use can cause a sensor to become "biofouled" over time such that the operational properties of the sensor may change. In particular, proteins may begin to develop on the sensor within minutes of insertion of the sensor into the tissue, which may cause the sensor to operate improperly. In view of the foregoing, there remains a need for circuits, compositions of matter, and methods which can be used to, inter alia, detect biomolecular concentrations in vivo.

SUMMARY OF THE INVENTION

Methods according to embodiments of the present invention can include providing labeled antibodies in vivo to tissue having antigens that specifically bind the labeled antibody. A first optical radiation is emitted into the tissue in vivo to provide excite the labeled antibody bound to the antigen in vivo. A second optical radiation that is emitted by the excited labeled antibody in response to the excitation thereof can be detected in vivo. In some embodiments, the labeled antibodies are fluorescently labeled antibodies.

In other embodiments, the step of providing can include releasing the labeled antibodies in vivo from a matrix material over time. In other embodiments, the step of providing can include releasing the labeled antibodies in vivo from a matrix material responsive to a control circuit located in vivo.

In some embodiments, the step of exciting can include emitting the first optical radiation through a bio-fouling tissue. In other embodiments, the step of detecting can include detecting the second optical radiation through a bio-fouling tissue.

Accordingly, labeled antibodies can bind antigens associated with tumor cells. A radiation source can be used to excite the labeled antibodies bound to the antigens. The labeled antibodies emit a second optical radiation in response to the excitation. A sensor can be used to detect a level of the optical radiation emitted by the labeled antibodies. The level of the second optical radiation can be used to determine the concentration of antigens present. The growth or proliferation of the tumor cells may be approximated from the concentration of antigen. Embodiments of the invention advantageously integrate the ability to probe fluorescently tagged entities with an implantable sensor platform, thus allowing accurate, real time determinations of antigen concentration in vivo.

DESCRIPTION OF EMBODIMENTS OF THE INVENTION

Figure 1:
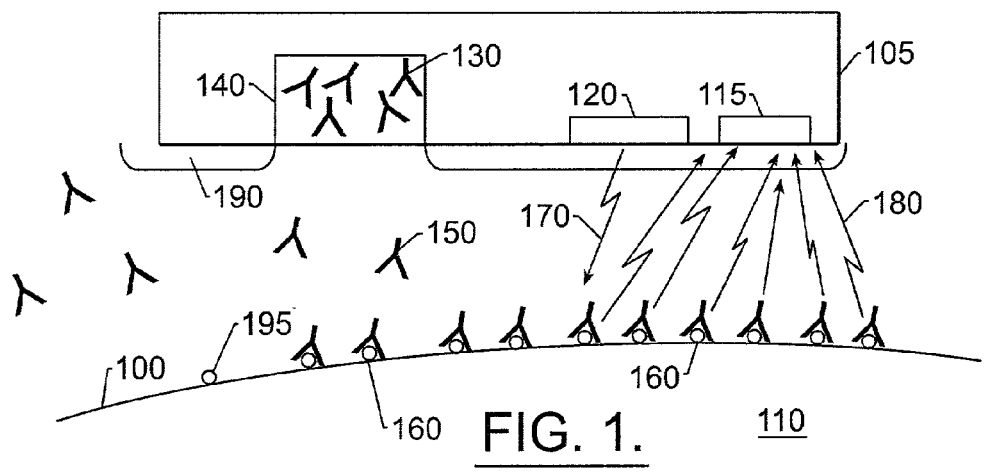
FIG. 1 is a schematic illustration of embodiments according to the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain layers, regions, or components may be exaggerated or enlarged for clarity.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. The term "tissue," as used herein, can include cells, organs, bodily fluids, and other biological matter in a biological sample or the body of a subject. For example, the term tissue can be used to describe cells, organs and/or other biological matter in a human body. The term "biomolecule" can include tumor specific antigens (TSA), such as proteins associated with particular types of tumor cells. It will be understood that the present invention may be used for in vivo use or for ex vitro use. It will also be understood that the term "in vivo" is specifically intended to encompass in situ applications.

In a preferred embodiment of the present invention, biomolecules (e.g., antigens) associated with hyperproliferative cells (including tumors, cancers, and neoplastic tissue, along with pre-malignant and non-neoplastic or non-malignant hyperproliferative cells) are detected. The term "tumor" is generally understood in the art to mean an abnormal mass of undifferentiated cells within a multicellular organism. Tumors can be malignant or benign. Preferably, embodiments of the inventions disclosed herein are used to detect biomolecules associated with malignant tumors. Examples of tumors, cancers, and neoplastic tissue associated with the biomolecules that can be detected by embodiments of the present invention include but are not limited to malignant tumors such as breast cancers; osteosarcomas; angiosarcomas; fibrosarcomas and other sarcomas; sinus tumors; ovarian, uretal, bladder, prostate and other genitourinary cancers; colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas. Biomolecules associated with premalignant and non-neoplastic or non-malignant hyperproliferative tissue include but are not limited to biomolecules associated with myelodysplastic disorders; cervical carcinoma-in-situ; familial intestinal polyposes such as Gardner syndrome; oral leukoplakias; histiocytoses; keloids; hemangiomas; psoriasis; and cells made hyperproliferative by viral infections (e.g., warts).

Although the present invention is described herein with reference to the detection of antigens associated with tumor and other hyperproliferative cells, the present invention may also be utilized for the measurement of glucose, cell necrosis byproducts, cell signaling proteins, and the like.

The embodiments of the present invention are primarily concerned with use in human subjects, but the embodiments of the invention may also be used with animal subjects, particularly mammalian subjects such as primates, mice, rats, dogs, cats, livestock and horses for veterinary purposes, and for drug screening and drug development purposes.

As used herein, the term "optical radiation" can include radiation that can be used to transmit signals in tissue, such as radiation in the visible, ultraviolet, infrared and/or other portions of the electromagnetic radiation spectrum.

Although the embodiments described herein refer to fluorescently labeled binding molecules (i.e., antibodies), it will be understood that the present invention may be used with any type label, including fluorescent labels (e.g., fluorescein, rhodamine), radioactive labels (e.g., $^{35}S$, $^{125}I$, $^{131}I$), bioluminescent labels (e.g., biotin-streptavidin, green fluorescent protein (GFP)), and enzyme labels (e.g., horseradish peroxidase, alkaline phosphatase).

It will also be understood that while embodiments described herein refer specifically to antibodies, the present invention may also be used with other molecules that bind the biomolecules to be detected. Furthermore, although the present invention is described with reference to detecting concentrations of antigens, the present invention may also be used to detect the concentration of any biomolecules whose detection is desired, including but not limited to proteins, polypeptides, nucleic acids, polysaccharides, and the like.

As used herein, the term "antibody" is understood to encompass all antibodies as that term is understood in the art, including but not limited to polyclonal, monoclonal, chimeric, and single chain antibodies, Fab fragments, and fragments produced by a Fab expression library. Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique. See, e.g., G. Kohler et al. (1975) *Nature* 256, 495-497; D. Kozbor et al. (1985) *J. Immunol. Methods* 81, 31-42; R. J. Cote et al. (1983) *Proc. Natl. Acad. Sci. USA* 80, 2026-2030; and S. P. Cole et al.(1984) *Mol. Cell Biol.* 62,109-120.

Chimeric antibodies may be produced according to methods set forth in, for example, S. L. Morrison et al. (1984) *Proc. Natl. Acad. Sci.* 81, 6851-6855; M. S. Neuberger et al. (1984) *Nature* 312, 604-608; and S. Takeda et al. (1985) *Nature* 314, 452-454). Alternatively, techniques described for the production of single chain antibodies may be adapted, using methods known in the art, to produce antigen-specific single chain antibodies. Antibodies may also be produced by inducing in vivo production in the lymphocyte population or by screening immunoglobulin libraries or panels of highly specific binding reagents as disclosed in the literature. See, e.g., R. Orlandi et al. (1989) *Proc. Natl. Acad. Sci,* 86, 3833-3837; and G. Winter et al. (1991) *Nature* 349,293-299. Antibodies with related specificity, but of distinct idiotypic composition, may be generated by chain shuffling from random combinatorial immunoglobulin libraries. See e.g., D. R. Burton (1991) *Proc. Natl. Acad. Sci.* 88,11120-11123).

Antibody fragments which contain specific binding sites for antigens can also be used. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity. See W. D. Huse et al. (1989) *Science* 254,1275-1281.

Fluorescence-based assays are well established for ex vitro studies and a number of fluorophores and tagged antibody systems are commercially available. An extensive list of commercially available pH-dependent fluorophores useful in the practice of the present invention can be found in R. P. Haugland, Chapter 23 ("pH Indicators") of *Handbook of Fluorescent Probes and Research Chemicals, Sixth Edition* (Molecular Probes, Inc. Eugene, Oreg., (1996), and HTML version located at www.probes.com).

According to embodiments of the present invention, fluorescently labeled binding molecules, such as antibodies, can be bound to biomolecules, such as antigens, associated with tumor cells. An optical radiation source can be used to excite the fluorescently labeled antibodies bound to the antigens. The fluorescently labeled antibodies emit a second optical radiation in response to the excitation. A sensor can be used to detect a level of the optical radiation emitted by the fluorescently labeled antibodies. The level of emitted optical radiation can be used to determine the concentration of antigens present. The concentration of antigen may then be correlated to the amount, or the presence, or the growth or proliferation behavior of the tumor cells based on known relationships between concentration of tumor specific antigen and these parameters, or according to relationships that may be determined by the skilled artisan.

FIG. 1 is a schematic illustration of embodiments according to the present invention that can be used to determine antigen levels of in vivo tumor tissue 110. The tumor tissue 110 may be characterized by a type of tumor specific antigen (TSA) 195 located at the surface 100 of the tumor tissue 110. For example, a TSA 195 may be found on the surface of cell tissue 110. In general, suitable biomolecules (i.e., TSAs) indicative of tumor cell proliferation are essentially independent of many of the biological, physiological, and/or environmental properties that are found in solid tumors. Although only a single surface of tissue 110 is shown, it will be understood that embodiments according to the present invention may be utilized to detect biomolecule concentrations for a plurality of tissue 110.

The phase of the tumor tissue 110 may be detected based on a concentration level of the TSA 195 at the surface 100. For example, a "growth" phase of the tumor may be characterized by relatively high concentrations of the TSA 195 and a "remission" phase may be characterized by relatively low concentrations of TSA 195.

A platform 105 is located in vivo proximate to the tumor tissue 110 and may or may not become bio-fouled with a bio-fouling tissue 190 over time. The platform 105 carries a matrix material 140 that can include fluorescently labeled antibodies 130 that are suspended in the matrix material 140. The matrix material 140 can be soluble so that the fluorescently labeled antibodies 130 can be released from the matrix material 140 over time. The matrix material 140 can be in the shape of a cylinder as shown, for example, in FIGS. 3 and 4. Other shapes may be used. The platform 105 can also include a telemetry system that transmits and receive signals to and from systems which are ex vitro.

The fluorescently labeled antibodies 130 are selected to specifically interact or bind with the TSA 195 that characterizes the tumor tissue 110, but is not associated with normal tissue. More than one TSA 195 may characterize a the tumor tissue 110. When the fluorescently labeled antibodies 130 are released from the matrix material 140, some of the fluorescently labeled antibodies 130 bind with the TSA 195 on the surface 100 proximate to the platform 105 to form a binding complex 160. The unbound fluorescently labeled antibodies 150 may dissipate over time to become remote from the platform 105.

An optical radiation source 120 emits a first optical radiation 170 that excites the fluorescent labels of the binding complexes 160 to a higher energy state. In one embodiment of the invention, the first optical radiation is emitted through a biofouling tissue 190. Once excited, the fluorescent labels of the bound complexes emit a second optical radiation 180. The respective wavelengths of the first optical radiation 170 and the second optical 180 may be selected to promote penetration of the bio-fouling tissue 190. The optical radiation source can be, for example, a laser diode, a high power Light Emitting Diode (LED), or the like, as described further herein.

An optical radiation detector 115 can detect the second optical radiation 180 through bio-fouling tissue 190 thereby avoiding some of the drawbacks associated with conventional techniques. A time interval between the emission of the first optical radiation 170 and detection of the second optical radiation 180 can be selected to allow the fluorescently labeled antibodies 130 to bind with the TSA 195 on the surface 100. The optical radiation detector 115 can be a photodiode or a phototransistor. Other devices as described further herein and/or known to those skilled in the art and may be also be used.

The optical radiation detector 115 can include an optical absorption filter to reduce the effects of background noise. The optical radiation source 120 and the optical radiation detector 115 can be separated by a shield that reduces the amount of the first optical radiation 170 that reaches the optical radiation detector 115. In some embodiments, the optical radiation detector 115 is located about 500 micrometers from the bound complexes 160. In other embodiments, the optical radiation detector 115 includes a lens that collects and focuses the second optical radiation 180 so that the separation between the optical radiation detector 115 and the bound complexes 160 may be increased.

The intensity of the second optical radiation 180 can be used to determine the concentration of the TSA 195. In particular, the TSA 195 that is proximate to the platform 105 may have fluorescently labeled antibodies 130 bound thereto. Accordingly, the fluorescent labels may emit the second optical radiation 180 after the excitation of the first optical radiation 170.

Figure 2:
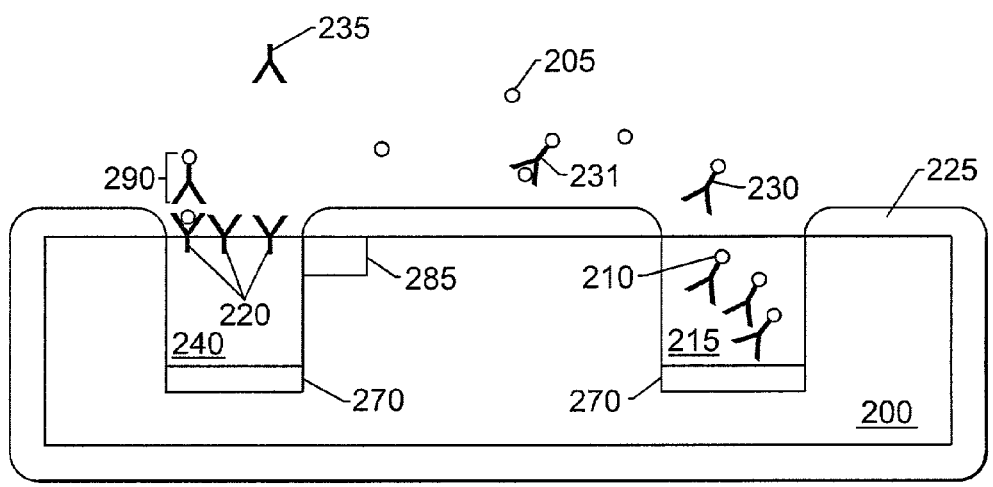
FIG. 2 is a schematic illustration of embodiments according to the present invention.

FIG. 2 is a schematic illustration of embodiments according to the present invention. According to FIG. 2, a platform 200 can be located in vivo proximate to tissue 290 that includes antigens 205. A bio-fouling tissue 225 may develop on portions of the platform 200 over time. The platform 200 can include first and second matrix materials 240 and 215, respectively. The first matrix material 240 can include unlabeled antibodies 220. The second matrix material 215 can include fluorescently labeled antibodies 210. In some embodiments, additional matrix materials can be used. As described herein, the matrix materials may include different concentrations of antibodies and/or mixtures of antibodies wherein some antibodies may be labeled and others may not be labeled.

The unlabeled and fluorescently labeled antibodies 220, 210 can be released continuously over time or in phases as described herein. The release of the respective antibodies may be out of phase with respect to each other. For example, unlabeled antibodies 220 may be released during a first time interval and the fluorescently labeled antibodies 210 may be released during a second time interval. The antibodies may also be released using an apparatus 270 coupled to the respective matrix material, as described further herein. The apparatus 270 coupled to each matrix material may be different. In some embodiments, the apparatus 270 may be used to control the rate of release of the unlabeled and/or labeled antibodies. The use of a controlled release strategy can be employed to provide a continuous source of fluorescently-labeled antibody 230, which can be advantageous in the dynamic biological environment in which the platform 200 must function.

The unlabeled antibodies 220 are released into the tissue 290 to provide free unlabeled antibodies 235. The fluorescently labeled antibodies 210 are released to provide free fluorescently labeled antibodies 230. Some of the free fluorescently labeled antibodies 230 bind to the antigens 205 to provide bound antigens 231. Some of the bound antigens 231 become bound to the unlabeled antibodies 220 at the surface of the second matrix material 240 to provide bound structures 290 at the surface of the second matrix material 240. An optical radiation emitter/detector 285 is adjacent to the second matrix material 285 and can be used to excite the bound structures 290 and detect a signal as discussed above.

Figure 3:
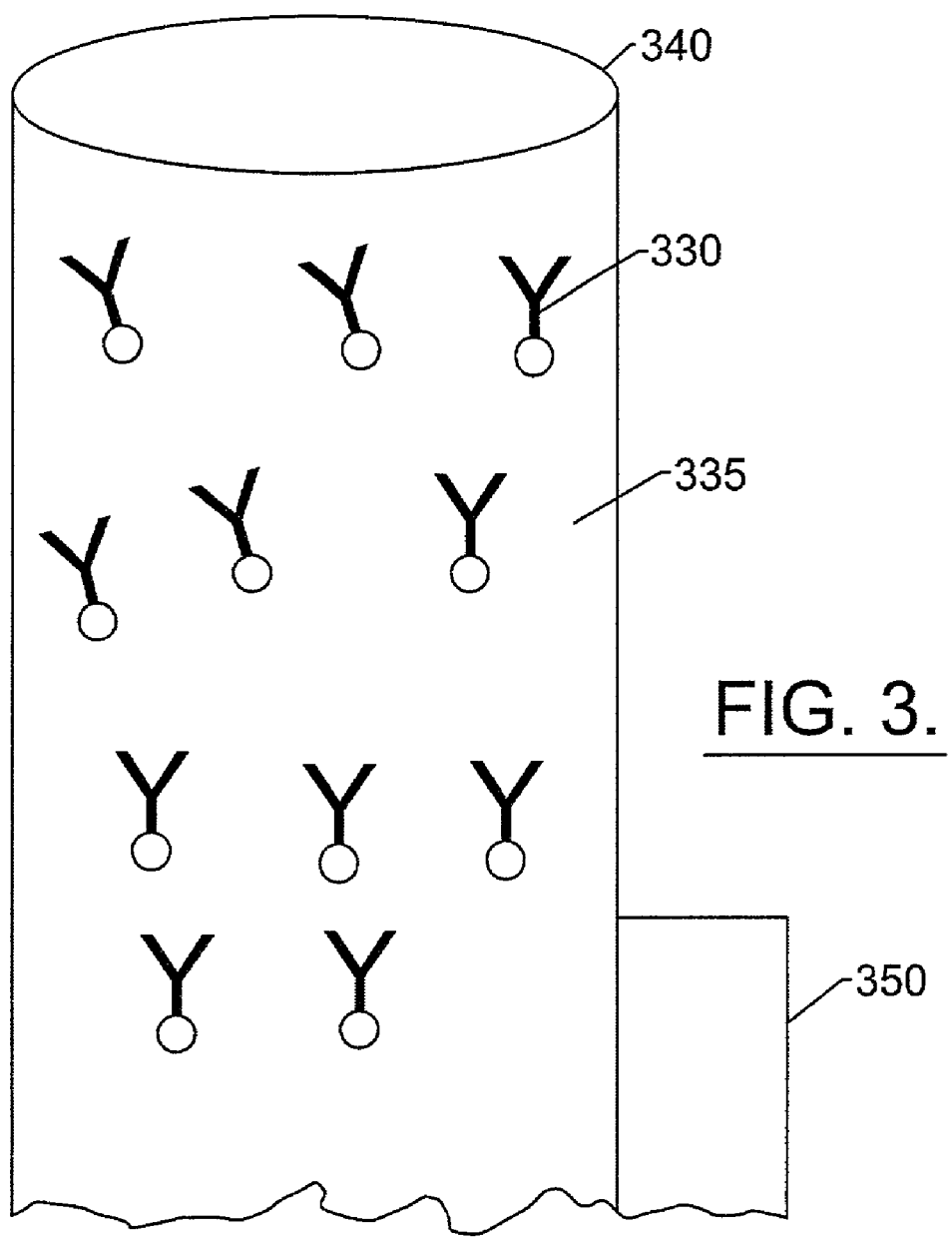
FIG. 3 is a schematic illustration of matrix compositions of matter according to the present invention.

FIG. 3 is a schematic illustration of compositions of matter according to the present invention. According to FIG. 3, fluorescently labeled antibodies 330 are released from a matrix material 335 over time. The matrix material can be selected based on factors such as biocompatibility, time release characteristics, degradation, interaction with the fluorescently labeled antibodies 330 suspended therein, lack of autofluorescence, etc.

It will be understood that other fluorescently labeled antibodies may be included in the matrix material 335 to provide a mixture of different types of antibodies. The term "different types of antibodies" will be understood to meant that one type of antibody may have more than kind of label, i.e., label A and label B. Alternatively, more than one type of antibody (i.e., antibody A and antibody B) may have the same label. For example, the matrix material 335 can include type A and type B fluorescently labeled antibodies 330. Moreover, the A and B type fluorescently labeled antibodies 330 may have different concentrations. For example, the A type fluorescently labeled antibodies 330 can comprise 20% of the fluorescently labeled antibodies 330 and the type B fluorescently labeled antibodies 330 can comprise 80% of the fluorescently labeled antibodies 330. Additional types of fluorescently labeled antibodies 330 may also be included in varying concentrations.

It is preferable that the matrix material 335 not react with or damage the fluorescently labeled antibodies 330 suspended therein. It is also preferable that the matrix material 335 not promote bio-fouling at the interaction surface 340 so that the fluorescently labeled antibodies 330 may be released over time without undue interference. The matrix material 335 may comprise one or more of several polymers. The choice of polymer can be determined empirically as encapsulation, degradation and release characteristics of polymers in tissue may vary from subject to subject, or from cell type to cell type, or from sample to sample, and the like. Suitable biodegradable polymers can be based on hydrolysis of ester linkages in the polymer, and a variety of polymers of this type are commercially available and well characterized. Many of these polymers degrade into small, non-toxic molecules. Some of the most common biodegradable polymers are poly(lactic acid) and poly(glycolic acid). Fried, Joel R. Polymer Science and Technology, Englewood Cliffs, N.J., Prentice Hall, 1995, pp. 246-249. In some embodiments according to the present invention, the matrix material 335 is a mixture of different materials such as a combination of polylactic acid and polyglycolic acid. The different materials can occur in a range of concentrations. For example, the matrix material 335 can comprise between about 0 and about 50% polylactic acid and/or between about 10 and about 50% polyglycolic acid.

In some embodiments, time release of the fluorescently labeled antibodies 330 may be controlled by selecting the matrix material 335 based on the biocompatibility of the material 335 with the antibody or biomolecule to be detected, polymer type, polymer structure (e.g., the physical size and porosity of the polymer release bead), the molecular weight of the matrix material 335, the porosity of the matrix material 335, and/or other material parameters.

In other embodiments, the matrix material 335 may be coupled to an apparatus 350 that can affect the rate at which the matrix material 335 releases the fluorescently labeled antibodies 330. For example, the apparatus 350 can be a piezoelectric circuit that vibrates the matrix material 335, thereby causing the fluorescently labeled antibodies 330 to be released at varying rates. Although several parameters (e.g., polymer structure, molecular weight, porosity, etc.) are available to control the rate and time course of release, other techniques for controlling release may be used. For example, the polymer may be mounted on top of a piezoelectric element, whereby the actuation of the element (e.g., mechanically shaking the polymer with a sinusoidal input to the piezoelectric) increases the rate of release. Another option for modulating release rate is to blend the matrix material 335 with an electrically conducting polymer (e.g., polypyrrole) and, by oxidizing and reducing the polymer electrochemically, modulate the porosity of the blend (Konturi et al., "Polypyrrole as a model membrane for drug delivery", *Journal of Electroanalytical Chemistry*, 1998, 453(1-2), 231-238, Hepel, M. et al., "Application of the electrochemical quartz crystal microbalance for electrochemically controlled binding and release of chlorpromazine from conductive polymer matrix", *Microchemical Journal,* 1997, 56, 54-64, Yano, S. et al., "Extracellular release of a recombinant gene product by osmotic shock from immobilized microalga in electroconductive membrane" *Bioelectrochemistry and Bioenergetics,* 1996, 39, 89-93, Bidan et al., "Incorporation of Sulfonated Cyclodextrins into Polypyrrole—An Approach for the Electro-controlled delivering of Neutral-Drugs", *Biosensors & Bioelectronics,* 1995, 10, 219-229, Hepel, M. et al., "Electrorelease of Drugs from Composite Polymer-Films" *ACS Symposium Series,* 1994, 545, 79-97.

Figure 4:
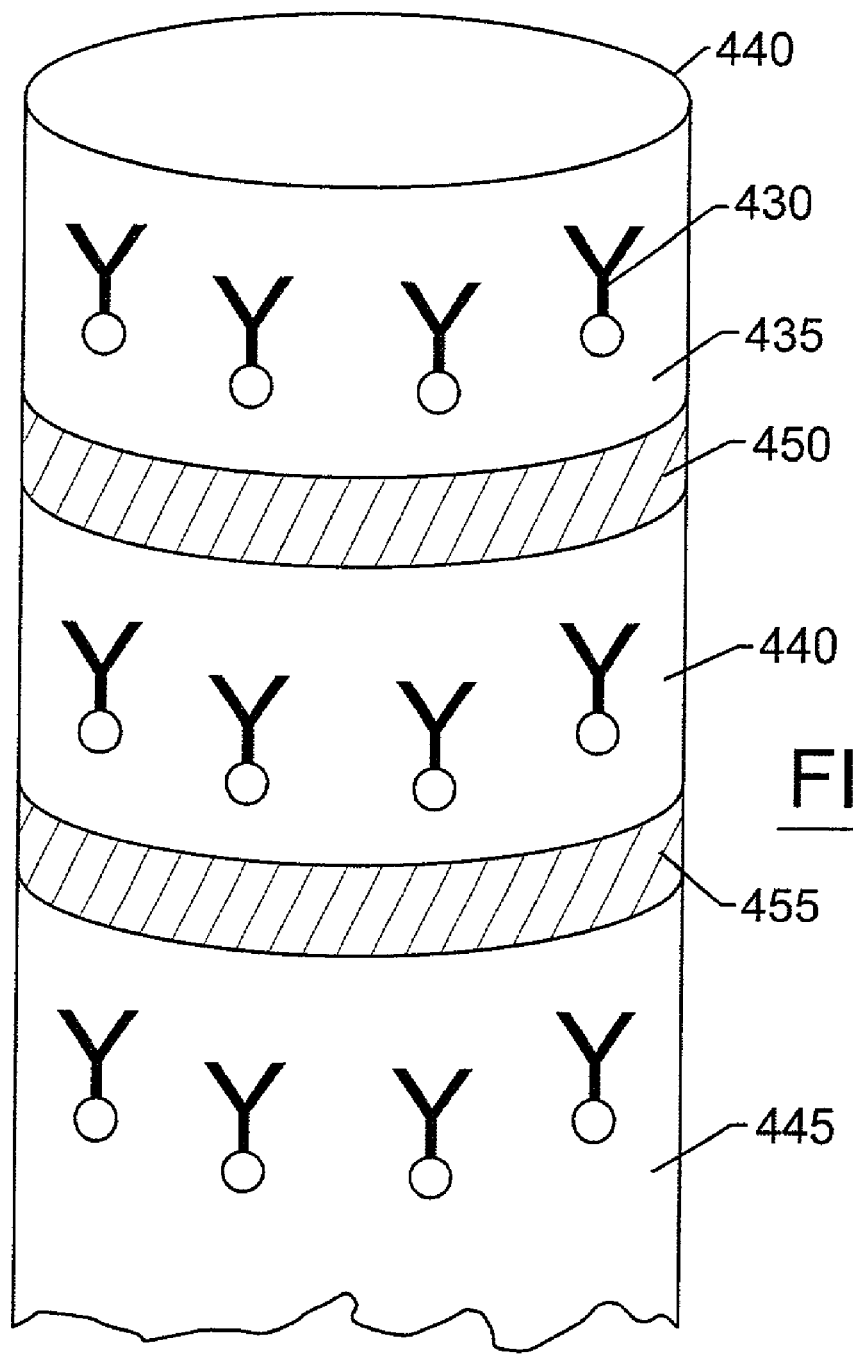
FIG. 4 is a schematic illustration of matrix compositions of matter according to the present invention.

FIG. 4 is a schematic illustration of compositions of matter according to the present invention. According to FIG. 4, fluorescently labeled antibodies 430 are released within the first, second, and third matrix material sections 435,440, 445. The first and second matrix material sections 435,440 are separated by a first separator material 450 that can be devoid of the fluorescently labeled antibodies 430. The second and third matrix material sections 440,445 are separated by a second separator material 455 that can be devoid of the fluorescently labeled antibodies 430. The different matrix material sections can provide for "pulses" of labeled material to be released at different times. In particular, after a barrier dissolves, the underlying matrix section can provide for a pulsed release of the labeled antibody. This could be used, for example, to measure a level of antigen expression over time. Moreover, the first, second, and third matrix materials sections 435,440,445 can each have different compositions of fluorescently labeled antibodies 430 to provide different rates of release over time.

Figure 5:
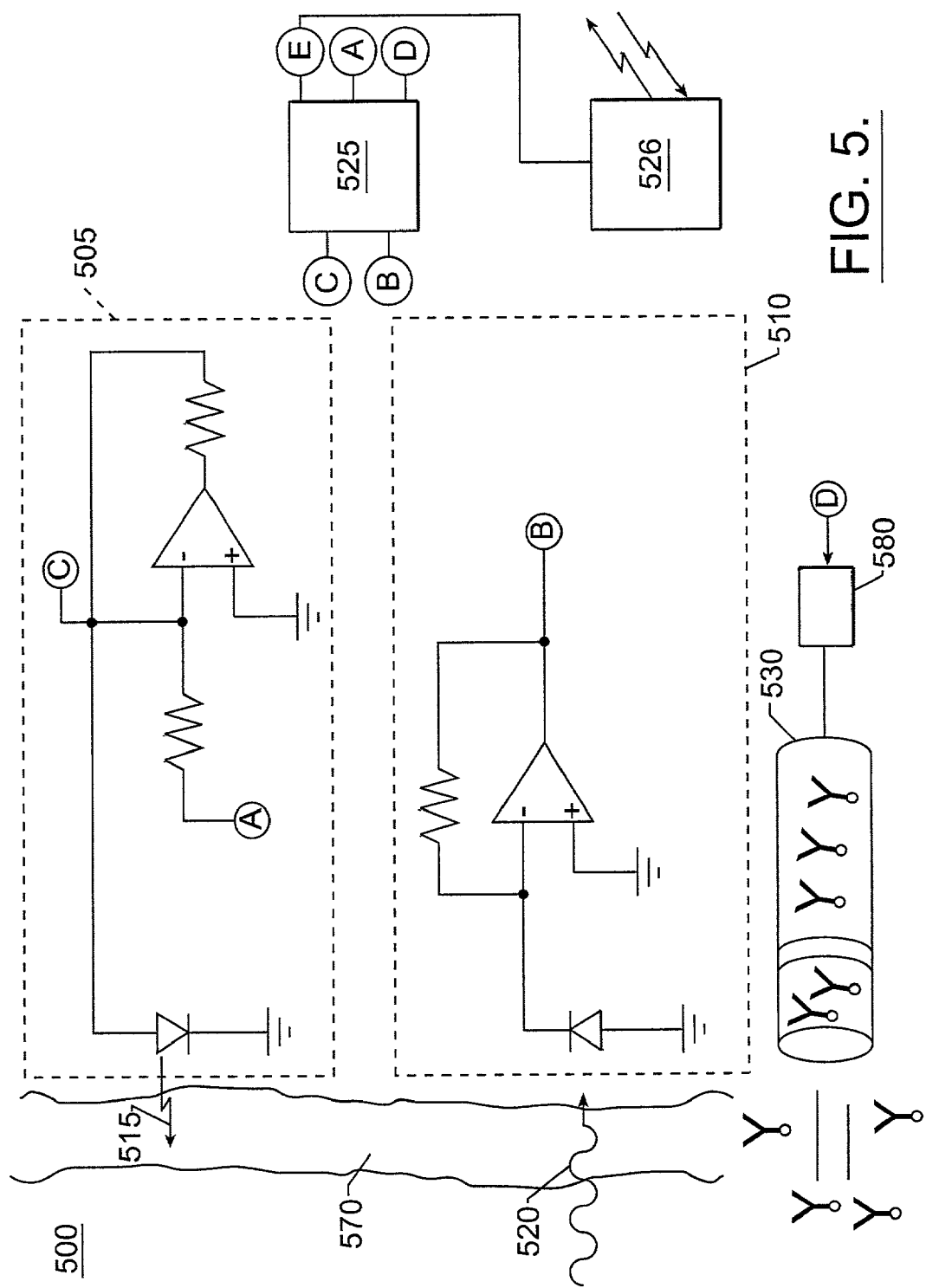
FIG. 5 is a circuit diagram that illustrates embodiments according to the present invention.

FIG. 5 is a diagram that illustrates embodiments of in vivo circuits and systems according to the present invention. A matrix material 530 includes the fluorescently labeled antibodies that are released in a tissue 500 as described, for example, in reference to FIGS. 3 and 4. The matrix material 530 can be coupled to an apparatus 580 that can vary the rate of release of the fluorescently labeled antibodies as described, for example, in reference to FIGS. 3 and 4.

An optical radiation source 505 can include an amplifier that responds to a control input A to provide an output current that passes through a high power light emitting diode that emits optical radiation 515. The optical radiation 515 can pass through a bio-fouling tissue 570 and excite the fluorescent labels on the fluorescently labeled antibodies.

The excited fluorescent labels can emit an optical radiation 520 that can pass through the bio-fouling tissue 570 to reach an optical radiation detector 510. For example, the optical radiation 520 impinges a photodetector. In response, the photodetector can generate a current that can be converted to a voltage level that represents the level of the optical radiation 520. In some embodiments according to the present invention, the photodetector is a photomultiplier. The optical radiation detector 510 can include an absorption filter to reduce background noise.

The optical radiation source 505, the optical radiation detector 510, and the matrix material 530 can operate in conjunction with a processor circuit 525. The processor circuit 525 can control the release of the fluorescently labeled antibodies from the matrix material 530 by controlling the apparatus 580 that, for example, vibrates the matrix material 530 to vary the rate of release of the fluorescently labeled antibodies.

The processor circuit 525 can provide an input to the optical radiation source 505. The processor circuit 525 can monitor an output signal C from the optical radiation source 505 to determine, for example, the power output thereof. Other functions may be monitored and/or controlled.

The processor circuit 525 can receive a voltage level B from the optical radiation detector 510 to determine, for example, the intensity of the optical radiation 520. The processor can provide an output E to a telemetry system (526). The telemetry system 526 can transmit/receive data to/from an ex vitro system (not shown). The ex vitro system can control the release of the fluorescently labeled antibodies by transmitting a signal into the body for reception by the in vivo system. The in vivo system can release fluorescently labeled antibodies in response to the signal from the ex vitro system. Other signals can be transmitted from the ex vitro system. In some embodiments, the transmitted/received data is digitally encoded. Other types of data transmission may be used.

The in vivo system can transmit data to the ex vitro system. For example, the in vivo system can transmit data associated with the intensity of the optical radiation 520. The in vivo system can transmit other data to the ex vitro system. Accordingly, the in vivo system can be implanted for in vivo use whereby the ex vitro system can control operations of the in vivo system including receiving data from the in vivo system without an associated invasive procedure.

In some embodiments, the in vivo system is powered remotely through the tissue in which it is implanted. For example, the in vivo system can include an inductor that provides power to the in vivo system via an inductively coupled power signal from the ex vitro system. In some embodiments, the in vivo system has a diameter of approximately 2 mm.

In the embodiments of the invention described above, a light emitting diode (LED) or laser diode (for greater excitation intensity) can be used as the excitation source and a photodiode can be used to detect the corresponding emission signal. Integral emission and absorption filters can be introduced as needed in the form of dielectric coatings on the diode elements. Light emitting diodes, and photodetectors are now commonly available. These devices can be extremely compact, with a laser diode being typically less than 100 µm. Thin film deposition and fiber optic technologies known to the skilled artisan permit the construction of extremely sharp optical filters.

An external sensor package for the optical implant apparatus described above may be about 2 mm×10 mm in the form of a rounded cylinder. This configuration may ease insertion into a subject when used in conjunction with a device similar to a biopsy needle. The standardization of package size and geometry may enable a diverse range of coatings such as diamond like carbon (DLC) or glasses of various compositions and plastics. The inner portion of the package can be used to provide a hermetic seal isolating the device from the effects of moisture and attack by the body.

In some embodiments, laser diodes are mounted on a heat sink and emit light from front and rear facets perpendicular to the circuit board. The optical power from the rear facet can be measured by a photodetector mounted on the opposite side of the circuit board. This permits feed back control of the optical power. On one side of the optical barrier dividing the cylinder, a signal photodiode receives the return fluorescence or the absorption signal to be ratioed, as in the case of oxygen measurements. An optical rejection filter can be deposited on the photodetector to reduce background noise. The telemetry coil, drivers and other electronics can be distributed on either side of the circuit board.

The embodiments of the invention described herein may afford effective baseline correction, a potentially important consideration in the practice of the present invention. Changes in diode laser output as a function of time can be accommodated through the use of standard photodiode feedback techniques. Measurements before and after insertion can be used to provide an initial baseline. This may be helpful in assessing background fluorescence and the degree of non-specific binding. The influence of external lighting as a parameter may also be assessed. The lifetime of the implant may be as long as six months or even more in some cases.

One advantage of this detection scheme is that it may be relatively resistant to the accretion of material on the outer surface of the sensor ("biofouling"). One aspect of the invention provides for emission and absorption wavelengths through whatever over layer covers the sensor surface. The circuit may also be coated with a biocompatible optical translucent layer. Although close proximity of the target fluorophore to the sensor is desirable, significant leeway is obtained for detection of signals away from the site of sensor implantation. As discussed herein, one embodiment includes a time-released, tagged antibody or event-activated hybridization reaction. Continuous monitoring of the implanted sensor is possible so that kinetics of the reaction can also be assessed.

In embodiments of the present invention, a lens system may or may not be present, but the detector is preferably placed in close proximity (e.g., about 500 micrometers) to the source of fluorescence. In this way, the detector may become the image plane. The sensor may alternatively be non-imaging and accordingly may be used as a binary-state detector for the presence or absence of fluorescent signal.

As disclosed above, according to embodiments of the present invention, fluorescently labeled antibodies can be coupled to antigens associated with tumor cells. An optical radiation source can be used to excite the fluorescently labeled antibodies coupled to the antigens. The fluorescently labeled antibodies emit optical radiation in response to the excitation. A sensor can be used to detect a level of the optical radiation emitted by the fluorescently labeled antibodies. The level of optical radiation can be used to determine the concentration of antigens present on the surface of the tissue. The concentration of antigens may then be correlated to the proliferative state or growth behavior of the tissue. In the drawings and specification, typical preferred embodiments and methods according to the present invention have been disclosed. Although specific terms have been used, they are used in a generic and descriptive sense only and not for purposes of limitation, the scope of the present invention being set forth in the following claims.

What is claimed:

1. A circuit for detecting biomolecules in vivo, the circuit comprising
   an optical radiation source configured for in vivo use that emits first optical radiation;
   an optical radiation detector configured for in vivo use that detects second optical radiation emitted by excited labeled binding molecules; and
   a processor circuit, coupled to the optical radiation source and the optical radiation detector,
   wherein the processor circuit is configured to release fluorescently labeled antibodies selected to bind with predetermined Tumor Specific Antigens (TSAs),
   the processor circuit is further configured to activate the in vivo optical radiation source after a predetermined first time interval after release of the fluorescently labeled antibodies, the predetermined first time interval selected to allow a first portion of the fluorescently labeled antibodies to bind with local available TSAs and a second portion of the fluorescently labeled antibodies to become remote from the circuit so that the first optical radiation excites the first portion of the fluorescently labeled antibodies bound with the local available TSAs and does not excite the second portion of the fluorescently labeled antibodies that become remote,
   the processor circuit is further configured to sense a voltage generated by the in vivo optical radiation detector after a second predetermined time interval, the second predetermined time interval being after emission of the first optical radiation has ceased.

2. A circuit according to claim 1, wherein the optical radiation source comprises a laser.

3. A circuit according to claim 1, wherein the optical radiation detector is selected from a group consisting of a phototransistor, a photodiode, and a photomultiplier.

4. A circuit according to claim 1, wherein the first optical radiation has a first frequency and the second optical radiation has a second frequency.

5. A circuit according to claim 4, wherein the first frequency is greater than the second frequency.

6. A circuit according to claim 1 further comprising:
   an emission filter coupled to the optical radiation source; and
   an absorption filter coupled to the optical radiation detector.

7. A circuit according to claim 1, further comprising:
   an inductor coupled to the processor, wherein the inductor provides power to the circuit in response to a power signal received from the ex vivo system.

8. A circuit according to claim 1, wherein the circuit is on a platform having a diameter of about 2 mm.

9. A circuit according to claim 1, wherein the signal is digitally encoded.

10. A circuit according to claim 1, wherein the circuit is on a platform coated with a biocompatible optical translucent layer.

11. A circuit according to claim 1 wherein the first and second optical radiation comprises first and second optical radiation at respective first and second wavelengths selected to promote transmission of the first and second optical radiation through a bio-fouling tissue on the optical radiation source and the optical radiation detector.

12. A circuit according to claim 1 wherein the circuit comprises an implantable circuit configured for in vivo implantation for at least six months.

13. A circuit according to claim 1 wherein the processor circuit is further configured to provide the signal for wireless transmission to the ex vivo system.

14. A circuit according to claim 1 further comprising:
   a piezoelectric circuit responsive to the processor circuit, wherein the piezoelectric circuit is configured to vibrate under control of the processor circuit to release the labeled binding molecules.

15. A circuit according to claim 1, wherein the processor circuit is further configured to control release of unlabled binding antibodies separate from the fluorescently labeled antibodies.

16. A circuit according to claim 15 wherein the processor circuit is further configured to release the unlabled binding antibodies during a first time interval and to release the fluorescently labeled antibodies during a second time interval.

* * * * *